United States Patent [19]

Konomura

[11] Patent Number: 4,682,599
[45] Date of Patent: Jul. 28, 1987

[54] BASKET FORCEPS ASSEMBLY FOR ENDOSCOPE

[75] Inventor: Yutaka Konomura, Hachioji, Japan

[73] Assignee: Olympus Optical Co., Ltd., Japan

[21] Appl. No.: 725,092

[22] Filed: Apr. 19, 1985

[30] Foreign Application Priority Data

Apr. 25, 1984 [JP] Japan ............................. 59-61845[U]
Apr. 27, 1984 [JP] Japan ............................. 59-63432[U]

[51] Int. Cl.⁴ ............................................ A61B 17/22
[52] U.S. Cl. ..................................... 128/328; 128/356
[58] Field of Search ................................ 128/328, 356

[56] References Cited

U.S. PATENT DOCUMENTS 2,707,958  5/1955  Davis ............................. 128/328 X
2,943,626  7/1960  Dormia .
3,316,910  5/1967  Davis ............................. 128/328 X

FOREIGN PATENT DOCUMENTS 978818    12/1975  Canada ............................. 128/356
2829159   1/1980   Fed. Rep. of Germany .
3206381   1/1983   Fed. Rep. of Germany .
56-109705 8/1981   Japan .

Primary Examiner—Michael H. Thaler
Attorney, Agent, or Firm—Ostrolenk, Faber, Gerb & Soffen

[57] ABSTRACT

A basket forceps assembly for use with an endoscope which includes a basket connected to a front end tip and which may be stowed into a sheath. A passage for supplying fluid is formed in either the sheath or the front end tip so as to provide a communication between the interior and the exterior of the sheath when the basket is withdrawn into the sheath and the front end tip is fitted therein. In this manner, fluid supply through the sheath is enabled when the front end tip is filled into the sheath.

13 Claims, 10 Drawing Figures

FIG. 1
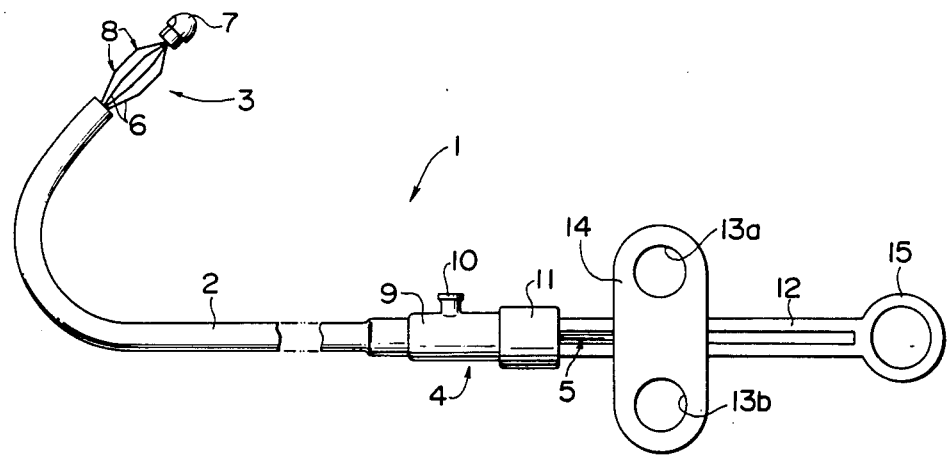
FIG. 2
FIG. 3
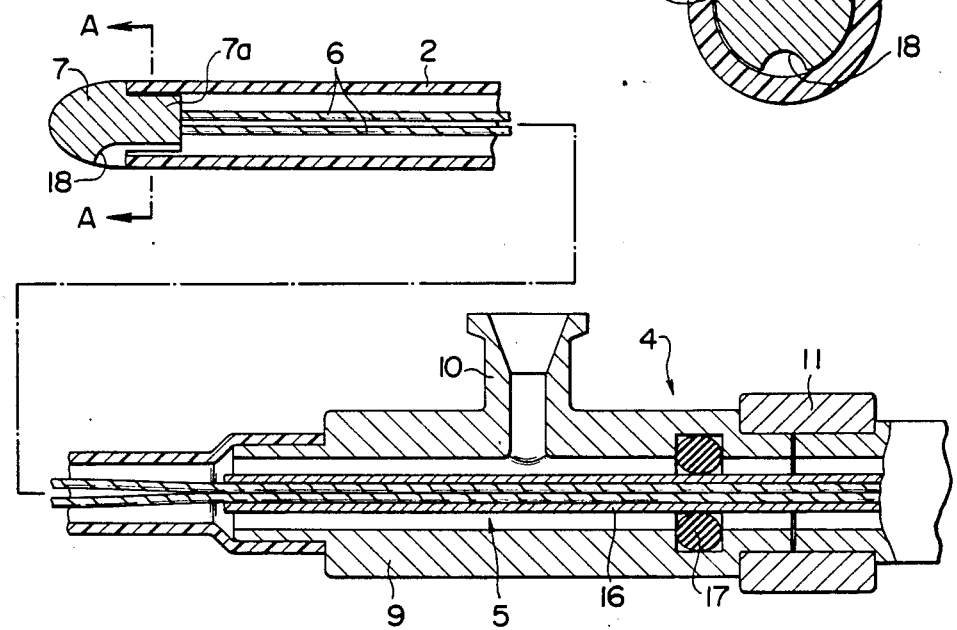

BASKET FORCEPS ASSEMBLY FOR ENDOSCOPE

BACKGROUND OF THE INVENTION

The invention relates to a basket forceps assembly for use with an endoscope, and more particularly, to an assembly which may be used in a medical endoscope to recover and remove any foreign matter located within a coelom such as a gallstone or ureteral calculus.

Recently, endoscopes have found extensive applications. Present endoscopes have an insertable portion of a reduced cross section and an increased length. The distal end of the insertable portion is adapted to emit light for illumination, thus enabling the observation of the interior of an illuminated coelom.

The insertable portion of the endoscope is capable of receiving a treatment instrument such as a baket forceps assembly for passage therethrough. The treatment instrument may be inserted through the insertable portion so as to enable the instrument to pick the tissue of an affected area located within the coelom for a detailed diagnosis of such part or to remove unwanted matters, such as calculi, which happen to form within the bile duct or ureter.

Where the calculus has grown to an increased size, a basket forceps assembly such as the device disclosed in Japanese Laid-Open Utility Model Application No. 109,705/1981, may be used. Specifically, a basket is formed on the distal end of the forceps assembly and is designed to receive a calculus therein, whereupon it may be closed to fracture and eliminate the calculus, by pulling a slider at the proximal end of the forceps assembly rearwardly.

A variety of such basket forceps assemblies are known, including an assembly of the type in which a water supply inlet is formed in the proximal end of the forceps assembly and is connected to the hollow interior of a flexible sheath through which an operating wire may be passed, thus allowing water or a fluid, such as a contrast agent, to be delivered through the front end of the flexible sheath. With this basket forceps assembly having a water outlet, there is no difficulty in maintaining a water supply when the individual resilient wires, which together form the basket, project beyond the front end of the sheath. However, when these wires are retracted to their stowed position within the flexible sheath and a front end tip to which the individual wires are fixedly connected is fitted into the front end of the sheath, the delivery of water or fluid is inhibited or rendered difficult, inasmuch as the opening in the front end of the sheath is effectively plugged by the front end tip. If an increased supply pressure is used, the water may be delivered in small quantities through a gap formed between the fitting parts. However, this method of delivering water is unreliable and adds to the burden of an operator who is operating the endoscope Additionally, it takes an increased length of time to complete the supply of a given amount of water. Additional disadvantages which are involved with supplying water under increased pressure include the likelihood that the front end tip may be disengaged from the free ends of the wires to be left within the coelom or that the force which caused the disengagement may also cause the tip or the expanding resilient wires to impact upon the internal wall of the coelom, which may then be injured. Even if the disengagement of the tip is prevented, the tip may still be driven forward under the increased water pressure, allowing a burst of water to be delivered at one time, making it difficult to maintain a reliable control over the amount of water supplied.

Water supply is permitted if the front end tip is maintained at a position projecting out of the front end of the sheath rather than blocking the latter. However, when the basket is not stowed within the sheath and the front end tip is not reliably secured in position as by fitting it in the front end of the sheath, such as when no calculus fracturing operation takes place or when a calculus is not held by the basket, the individual wires which form the basket are biased or urged to expand as they project, so that they may impact upon the internal wall of the coelom. Accordingly, maintaining the front end tip at its projecting position is undesirable for safety reasons.

In addition, if an operator is required to supply water when the free end tip is projecting, extreme care is required of the operator to note the degree to which the basket has been expanded or to watch if it is maintained in a condition to avoid any injury to the internal wall of the coelom. Thus, an increased burden on the part of the operator is necessarily required, which represents a major disadvantage.

SUMMARY OF THE INVENTION

In view of the foregoing, it is an object of the invention to provide a basket forceps assembly for use with an endoscope which permits fluid to be supplied when the front end tip is fitted into the front end of the sheath.

In accordance with the invention, a construction is employed in which the supply of fluid is enabled when the front end tip is fitted into the sheath. This permits an operator to supply any desired amount of fluid in a reliable and facilitated manner. The degree of safety which is involved with the supply of fluid is enhanced.

BRIEF DESCRIPTION OF DRAWINGS

FIG. 1 is a schematic side elevation of a basket forceps assembly for use with an endoscope constructed according to one embodiment of the invention;

FIG. 2 is a longitudinal section of essential parts of the basket forceps assembly shown in FIG. 1;

FIG. 3 is a cross section, to an enlarged scale, taken along the line A—A in FIG. 2;

DETAILED DESCRIPTION OF THE PREFERRED EMBODIMENTS

Figure 4:
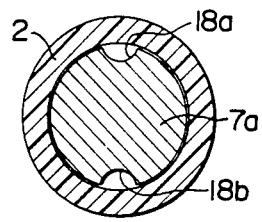
FIGS. 4 and 5 are similar cross sections to FIG. 3 of basket forceps assemblies according to other embodiments of the invention.

Referring to FIG. 1, there is shown a basket forceps assembly 1 for use with an endoscope according to one embodiment of the invention. The forceps assembly 1 essentially comprises a flexible hollow sheath 2 having a reduced cross sectional area and having a substantial length, a basket 3 which is disposed to be movable out of and into the front end of the sheath 2 for holding or fracturing a foreign matter, and a drive transmitting member 5 which if connected to the rear end of the basket 3 and passing through the sheath 2 to be introduced into an operating unit 4 at the rear end of the sheath 2.

The sheath 2 is formed of a synthetic resin or formed as a close pitch coil to exhibit flexibility so that it can be passed through a forceps receiving channel, formed within an endoscope, not shown, if the endoscope is flexed.

The basket 3 which is disposed to be movable out of the front end of the sheath 2 comprises a plurality of resilient wires 6, and a front end tip 7 to which the front ends of the individual resilient wires 6 are secured. The individual resilient wires 6 are bendably molded so as to be expanded or deployed into a basket form, by resiliently bending at bends 8, as shown in FIG. 1, whenever they are caused to project forwardly of the front end of the sheath 2.

The rear end of the sheath 2 is formed into a greater diameter so as to be fitted around the front end of a body 9 of the operating unit, and is secured thereto as by adhesive. A fitting 10 is formed in the lateral side of the body 9 and communicates with the hollow interior of the sheath 2 through the internal space within the body 9, and hence tubing, not shown, may be connected to the fitting 10 to permit water or fluid, such as a contrast agent, to be supplied from a source thereof.

The body 9 of the operating unit is connected through a coupling 11 to a guide member 12, which serves to guide a sliding movement through the body 9 of the drive transmitting the member 5. The guide member 12 is centrally formed with an elongate guide groove which receives the rear end of the drive transmitting member 5 therein. A slider 14 having a pair of lateral wings in which finger holes 13a, 13b are formed is fitted over the guide member 12, and is centrally formed in its front end with an opening, to which the rear end of the drive transmitting memeber 5 is secured. A finger tip 15 is formed on the rear end of the guide member 12. By engaging a pair of fingers with one of the finger holes 13a, 13b in the slider 14 and the finger tip 15, the slider 14 may be moved either forwardly or rearwardly, thus advancing or retracting the transmitting member 5 in the axial direction of the sheath 2. At the same time, the basket 3 connected the transmitting member 5 may be caused to project out of the front end of the sheath 2, as shown in FIG. 1, or may be retracted to its stowed position within the sheath 2, as shown in FIG. 2.

Referring to FIG. 2, the individual resilient wires 6, which form the basket 3, extend through the sheath 2 and then pass through the drive transmitting member 5 comprising an operating pipe 16, which surrounds the rearwardly extending portion of the basket 3. However, such drive transmitting member 5 may comprise a single or a plurality of wires or a pipe member connected to the rear end of the basket 3. The operating pipe 16 is disposed in abutting relationship with an O-ring 17, which is a seal member received in a peripheral groove formed in the body 9 at a position rearward of the fitting 10, thereby providing a water tight structure. Accordingly, if the operating pipe 16 is caused to advance or retract, water which is supplied through the fitting 10 or water which is contained within the sheath 2 is prevented from leaking through the rear end of the body 9.

The front end tip 7, to which the front ends of the individual resilient wires 6 are secured, is generally bullet-shaped, including a base 7a of an outer diameter which fits in the front end fo the sheath 2, and a semispherical or semi-ellipsoidal portion, which is coupled to the base. The semi-ellipsoidal portion has a diameter which is substantially equal to the outer diameter of the sheath 2. A notched groove 18 (see FIGS. 2 and 3) is formed through the semi-ellipsoidal portion and the base 7a at one location on the periphery thereof, the notched groove 18 extending lengthwise of the tip 7. In this manner, the notched groove 18 maintains a communication between atmosphere and the hollow interior of the sheath 2 even when the basket 3 is retracted into the sheath 2 or when the front end tip 7 serves as a plug which closes the front opening of the sheath 2, thereby enabling the water fed through the fitting 10 to be supplied through the notched groove 18.

In the operation of the embodiment described, it will be appreciated that when the basket 3 of the basket forceps assembly 1 which passes through a forceps receiving channel of an endoscope is retracted into the sheath 2 so that the front end tip 7 is fitted into the front end of the sheath 2 to close it, an operator is allowed to feed water from the fitting 10 without requiring any increased water pressure. In addition, there is reduced water pressure on the front end tip 7 as compared with a conventional basket forceps assembly in which a front end tip would completely plug the front end of a sheath and create a high water pressure. Thus, the invention facilitates water supply and reduces the burden on the operator who feeds water while assuring that any desired amount of water may be fed into the coelom through the notched groove 18. Because the water supply is achieved without causing the basket 3 to project out of the sheath, the likelihood that the bends 8 of the expanded resilient wires 6 may injure the internal wall of the coelom, as occurs in the prior art, is avoided, thus achieving the supply of water with a higher level of safety.

Figure 5:
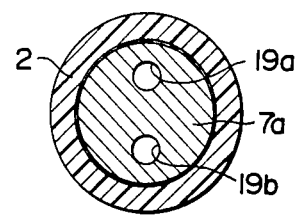

While a single notched groove 18 is formed in the described embodiment to provide a fluid supply passage in the front end tip 7, it will be understood that a pair of notched grooves 18a, 18b as shown in FIG. 4 or more notched grooves may be provided. Instead of providing notched grooves 18a, 18b, through openings 19a, 19b may be formed to extend through the front end tip 7 to provide a passage for supplying fluid, as illustrated in FIG. 5. These openings 19a, 19b may extend from the rear end face of the base 7a to the front end face of the tip completely, or alternatively may extend from the rear end face of the base 7a to the lateral surface of the semi-ellipsoidal portion. The number of such openings is not limited to two, but a single opening or a plurality of openings may be formed. Finally, a notched groove and a through opening may be provided in combination.

Instead of providing the notched grooves, 18a, 18b or through openings 19a, 19b in the front end tip 7 as shown in the embodiments described above, a notched groove or a through opening may be formed in the sheath 2 to provide a fluid supply passage. Such embodiments will now be described.

Figure 6:
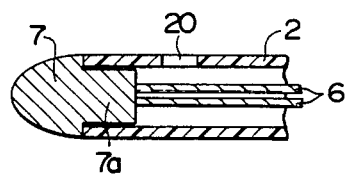
FIGS. 6 and 7 are a longitudinal section and a side elevation of the distal end portion of a basket forceps assembly according to a further embodiment of the invention.
Figure 7:
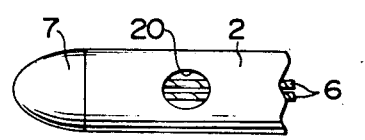

Referring to FIGS. 6 and 7, a through opening 20 is formed in the sheath 2 at a point slightly rearward of its region where the front end tip 7 is fitted. When the wires 6 which form the basket 3 (see FIG. 1) are retracted into the sheath 2 or the front end tip 7 serves as a plug which closes the front end opening of the sheath 2, a communication is maintained between the interior of the sheath 2 and the exterior through the opening 20. Accordingly, water from the fitting 10 (FIG. 1) can be fed through the opening 20. Again, the water supply is achieved under a reduced water pressure upon the front end tip 7, thus decreasing the burden on the part of an operator while assuring that any desired amount of water may be fed.

Figure 8:
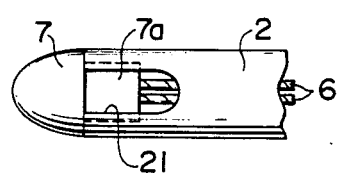
FIGS. 8 to 10 are side elevations of the distal end portion of basket forceps assemblies according to additional embodiments of the invention.

While a single opening 20 is formed in this embodiment, it will be apparent that a plurality of such openings may be formed. Also, such opening may be in the form of a notched elongate slot 21 which extends from the front edge of the sheath 2 to a rear portion thereof, as shown in FIG. 8. A plurality of such elongate slots 21 may be provided. Alternatively, the through opening 20 and the elongate slot 21 may be used in combination. As a further alternative, the notched groove 18 or through opening 19 (19a, 19b) may be formed in the front end tip 7 while the through opening 20 or the notched elongate slot 21 may be formed in the sheath 2 simultaneously.

Figure 9:
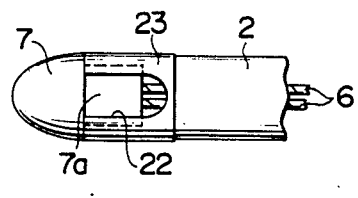
Figure 10:
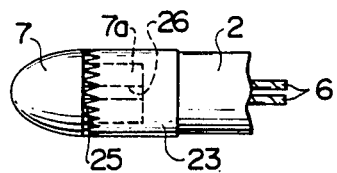

Instead of fitting the front end tip 7 directly on the front end of the flexible sheath 2 as shown in the described embodiments, an annular hard member 23, for example, may be mounted on the front end of the sheath 2 to increase its strength, causing the individual resilient wires 6 to abut against the hard member as they expand during the repeated projection and retraction of the basket 3. In this manner, the possibility that the front end of the sheath 2 may be damaged can be reduced. In addition, the provision of the hard 23 may improve the strength which can be relied upon when fracturing foreign, such as calculi. In such instance, a notched elongate slot 22 as shown in FIG. 9 or an opening of any desired configuration, either alone or a plurality thereof, may be formed in the hard member 23 which is fitted over the sheath 2 at a location where a communication between the interior and the exterior of the sheath 2 is obtained when the front end tip 7 is fitted therein. Alternatively, a series of continuously extending, serrated notches 25 may be formed along the front edge of the hard member 23, as shown in FIG. 10, thereby facilitating a fracture of a foreign matter picked from the coeloma while it is held by the basket (see FIG. 1). In this instance, a notched groove 26 is formed on the periphery of the base 7a of the front end tip 7, for example, so that a fluid supply path is provided when the front end tip 7 is fitted into the hard member 23 located on the front end of the sheath 2, thus providing a communication between the interior of the sheath 2 and the notch 25. Additionally, the rear end face of the front end tip 7 may be provided with projections (not shown) which effectively help a fracturing operation.

It will also be noted that a cock may be disposed within the fitting 10 which is formed in the operating unit 4 to interrupt a communication between the inside and the outside of the fitting 10 in a simple manner whenever water supply is not required. In addition, the fluid supply passage may also be utilized to withdraw water or other fluid. Additionally, such passage may also be utilized to supply or withdraw a gas.

It should be understood that the specific configuration of the resilient wires 6 as having a pair of bends 8 is not a limitation.

Finally, it should be understood that the invention is equally applicable to a basket forceps assembly having an operating unit of a configuration other than that shown in FIG. 1, and that the basket forceps assembly of the invention can also be utilized for recovery of foreign matters other than calculi.

What is claimed is:

1. A basket forceps assembly for use with an endoscope, comprising:

a flexible hollow sheath which can be passed through an insertable portion of an endoscope, said sheath having a front end, a hollow interior and an exterior;

a basket formed of a plurality of resilient wires, said basket being disposed so as to be movable into and out of the front end of said sheath and being adapted to hold foreign matter grasped therein;

a human actuable operating means connected to said basket so as to enable an operator to move said basket into and out of the front end of said sheath; and a front end tip which is secured to said basket and adapted to tightly fit the front end of said sheath when said basket has been fully retracted into said sheath, said front end tip including a base that is fully disposed within said sheath when said basket is fully retracted into said sheath;

said front end tip having a passage formed therein which maintains communication between the hollow interior and the exterior of said sheath at a location forward of said base when the front end tip is tightly fitted into the front end of said sheath.

2. A basket forceps assembly according to claim 1 in which the passage in said front end tip comprises a notched groove formed in a part of the outer periphery of the front end tip.

3. A basket forceps assembly according to claim 1 in which the passage in said front end tip is formed by an opening which extends through the front end tip.

4. A basket forceps assembly according to claim 1, 2 or 3 in which an additional passage is formed in said front end tip; said additional passage and said passage being of essentially the same construction and performing the same function in the same manner.

5. A basket forceps assembly according to claim 1 which further comprises an annular hard member which is fitted over and secured to the front end of said sheath.

6. A basket forceps assembly according to claim 1 in which said passage extends for at least the length of said base.

7. A basket forceps assembly according to claim 6 in which said base has a rear surface, and said passage extends forward from the rear surface.

8. A basket forceps assembly according to claim 7 in which the sheath is provided with a passage which maintains communication between the interior and exterior of the sheath when the front end tip is tightly fitted into the front end of the sheath; said passage in said sheath comprises an opening formed in said sheath at a location toward the front end of said sheath.

9. A basket forceps assembly according to claim 8 in which an additional passage is formed in said front end tip; said additional passage and said passage in said front end tip being of essentially the same construction and performing the same function in the same manner.

10. A basket forceps assembly according to claim 7 in which the sheath is provided with a passage which maintains communication between the interior and exterior of the sheath when the front end tip is tightly fitted into the front end of the sheath; said passage in said sheath comprises a notch formed in said sheath so as to extend from a front end face of the front end of said sheath along a wall thereof to a point rearward of said base.

11. A basket forceps assembly according to claim 10 in which an additional passage is formed in said front end tip; said additional passage and said passage in said front end tip being of essentially the same construction and performing the same function in the same manner.

12. A basket forceps assembly according to claim 7 in which an additional passage is formed in said front end tip; said additional passage and said passage being of essentially the same construction and perfoming the same function in the same manner.

13. A basket forceps assembly according to claim 1 in which the location is disposed immediately adjacent the front end of said sheath.

* * * * *